(12) United States Patent
Murugan et al.

(10) Patent No.: US 9,199,930 B2
(45) Date of Patent: Dec. 1, 2015

(54) PROCESS FOR THE PREPARATION OF (S)-2-ETHYL-N-(1-METHOXYPROPAN-2-YL)-6-METHYL ANILINE

(71) Applicant: Council of Scientific and Industrial Research, New Delhi (IN)

(72) Inventors: Muthukrishnan Murugan, Pune (IN); Prashant Pramod Mujumdar, Pune (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 14/426,452

(22) PCT Filed: Sep. 6, 2013

(86) PCT No.: PCT/IN2013/000540
§ 371 (c)(1),
(2) Date: Mar. 6, 2015

(87) PCT Pub. No.: WO2014/037962
PCT Pub. Date: Mar. 13, 2014

(65) Prior Publication Data
US 2015/0225340 A1    Aug. 13, 2015

(30) Foreign Application Priority Data
Sep. 6, 2012  (IN) .......................... 2768/DEL/2012

(51) Int. Cl.
*C07C 213/02* (2006.01)
*C07D 203/14* (2006.01)

(52) U.S. Cl.
CPC ............ *C07D 203/14* (2013.01); *C07C 213/02* (2013.01)

(58) Field of Classification Search
CPC .......................... C07C 213/023; C07D 203/14
See application file for complete search history.

(56) References Cited

U.S. PATENT DOCUMENTS

| 5,886,255 | A | 3/1999 | Aronstam | |
|---|---|---|---|---|
| 8,461,386 | B2 * | 6/2013 | Shroff et al. | 564/209 |
| 8,748,660 | B2 * | 6/2014 | Murugan et al. | 564/158 |

FOREIGN PATENT DOCUMENTS

| WO | WO-2006003194 A1 | 1/2006 |
|---|---|---|
| WO | WO-2014037962 A1 | 3/2014 |

OTHER PUBLICATIONS

"International Application Serial No. PCT/IN2013/000540, International Preliminary Report on Patentability mailed Mar. 10, 2015", 7 pgs.

"International Application Serial No. PCT/IN2013/000540, International Search Report mailed Jan. 3, 2014", 3 pgs.

"International Application Serial No. PCT/IN2013/000540, Written Opinion mailed Jan. 3, 2014", 6 pgs.

* cited by examiner

*Primary Examiner* — Shailendra Kumar
(74) *Attorney, Agent, or Firm* — Schwegman Lundberg & Woessner, P.A.

(57) ABSTRACT

Disclosed herein a novel, process for the preparation of (S)-2-ethyl-N-(1-methoxypropan-2-yl)-6-methyl aniline [(S)-1]. Particularly, the invention relates to the synthesis of (S)-2-ethyl-N-(1-methoxypropan-2-yl)-6-methyl aniline with excellent selectivity starting from commercially available enantiopure (R)-epichlorohydrin [(R)-2] via formation of aziridine intermediate [(S)-4].

9 Claims, 6 Drawing Sheets

PROCESS FOR THE PREPARATION OF (S)-2-ETHYL-N-(1-METHOXYPROPAN-2-YL)-6-METHYL ANILINE

CROSS-REFERENCE TO RELATED APPLICATIONS

This application is a U.S. National Stage Filing under 35 U.S.C. §371 from International Application No. PCT/IN2013/000540, filed on 6 Sep. 2013, and published as WO2014/037962 on 13 Mar. 2014, which claims the benefit under 35 U.S.C. §119 to Indian Application No. 2768/DEL/2012, filed on 6 Sep. 2012, which applications and publication are incorporated herein by reference in their entirety.

TECHNICAL FIELD OF INVENTION

The present invention relates to a process for the preparation of (S)-2-ethyl-N-(1-methoxypropan-2-yl)-6-methyl aniline. Particularly, the invention relates to the synthesis of (S)-2-ethyl-N-(1-methoxypropan-2-yl)-6-methyl aniline with excellent selectivity from enantiopure (R)-epichlorohydrin via formation of aziridine intermediate.

BACKGROUND AND PRIOR ART

Metolachlor is a derivative of aniline and is a member of the chloroacetanilide herbicides used worldwide for control of broad-leaf weeds in corn, soybean, peanuts, sorghum, and cotton. Chemically metolachlor is known as 2-chloro-N-(2-ethyl-6-methylphenyl)-N-(2-methoxy-1-methyl) acetamide.

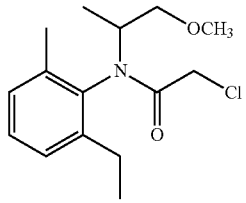

Racemic Metolachlor

Metolachlor comprises four stereoisomers, two of which are inactive. The isomerism is based on a combination of a chiral center in the aliphatic side chain and a chiral axis between the phenyl group and the nitrogen atom. The originally formulated metolachlor was applied as a racemate, a 1:1 mixture of the (S)- and (R)-stereoisomers. It later came to be known that about 95% of the herbicidal activity of metolachlor exists in the two 1-S diastereomers. This meant that (S)-enantiomers provided high herbicidal activity than the (R)-enantiomers. Hence, work was initiated to provide a feasible enantioselective process resulting in enriching the isomeric ratio in favor of the (S)-enantiomers to increase the biological activity of the herbicide.

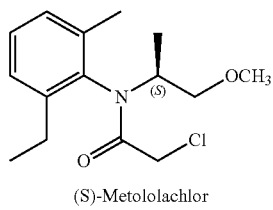

(S)-Metololachlor

Initially, the search was for a suitable enantioselective catalyst which could produce (S)-metolachlor with high ee. Article titled "Enantioselective catalysis for agrochemicals. The case histories of (S)-metolachlor, (R)-metalaxyl and clozylacon" by Hans-Ulrich Blaser et. al in Topics in Catalysis, 4, (1997) 275-282, discusses the hydrogenation of both MEA and DMA imine with Rh diphosphine complexes. Under ambient conditions enantioselectivities in the range of 3-50% were obtained. Using $[Rh(nbd)Cl]_2$/cycphos at $-25°$ C., imine hydrogenation was achieved up to 69% enantiomeric excess which was far too low for an industrial application. Due to low reactivity of Rd complexes as enantioselective catalysts, the said article further discusses the synthesis of herbicide (S)-metolachlor (trade name DUAL MAGNUM) by enantioselective hydrogenation of an imine intermediate using iridium ferrocenyl-diphosphine catalyst with an enantioselectivity of 80%. An attempt to prepare all the three isomers of metolachlor-enamide with Rh or Ru/binap catalysts is also described with very little success.

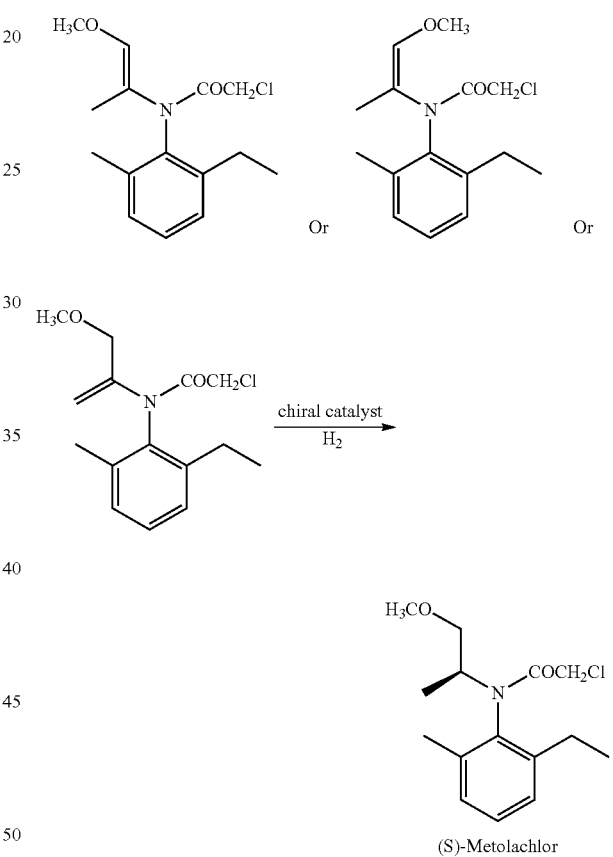

(S)-Metolachlor

Syngenta had identified the increased biological activity of the S-isomer pair of metolachlor and the technology to separate the isomers in 1982. However, separation as opposed to selective synthesis is inherently wasteful because it requires the disposal of the large volume of the less herbicidally active R-isomer pair that is not needed in S-metolachlor.

U.S. Pat. No. 5,886,225 (Jalett Hans-Peter et al.) relates to a process for the hydrogenation of imines of formula (I) with hydrogen under elevated pressure in the presence of iridium catalysts and with or without an inert solvent, wherein the reaction mixture contains hydrogen iodide to obtain amines of the formula (II). The optical yield ee is about 75-78%.

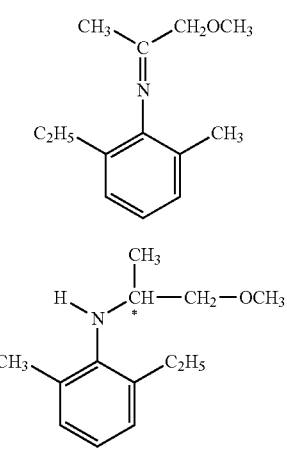

(I)

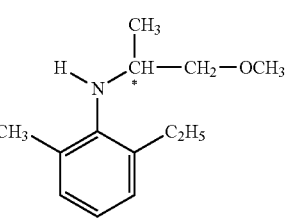

(II)

U.S. Pat. No. 6,822,118 (Hans-Pèter Jalett et al.) pertains to a process for the hydrogenation of imines with hydrogen under elevated pressure in the presence of iridium catalysts, Ir/ferrocenyl-diphosphine with or without an inert solvent, wherein the reaction mixture contains an ammonium or metal chloride, bromide or iodide and additionally an acid. The hydrogenation process yields amines with enantiomeric excess about 80%.

WO2009/136409 (Jaidev R. Shroff, et al.) relates to asymmetric hydrogenation of imine of Formula III under elevated pressure in presence of a catalyst system comprising a ligand complexed to a metal selected from iridium and rhodium or a salt thereof to obtain amine of Formula IV with greater than or equal to 76% ee, useful for the preparation of S-metolachlor. The invention further discloses that the process may optionally further comprises the addition of additive.

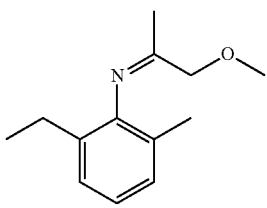

III

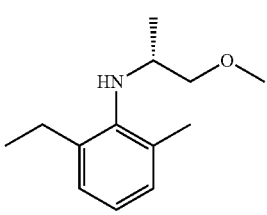

IV

WO2006/003194 (Pugin, Benoit et al.) provides a process for the preparation of secondary amines by hydrogenation of ketimine in presence of iridium complex with chiral ferrocene tetraphosphines in which a secondary phosphine group and 1-secondary phosphinalk-1-yl are bound to each cyclopentadienyl ring in ortho positions. The configurational isomer obtained is preferably S-enantiomer where enantiomeric excess (ee) is at least 50%, preferably at least 60% and particularly at least 70%.

EP0605363 (Bader Rolf et al.) discloses a process for the preparation of 2-alkyl-6-methyl-N-(1'methoxy-2'-propyl)- aniline by catalytic reductive alkylation, wherein at least one mole equivalent of methoxyacetone is reacted with one mole equivalent of 2-alkyl-6-methyl-aniline in a liquid medium without an additional solvent, in the presence of a platinized carbon catalyst and hydrogen and in the presence of an acid co-catalyst under a hydrogen pressure of between $2 \times 10^5$ and $1 \times 10^6$ Pa at a temperature between 20° and 80° C., characterized in that the reaction mixture contains water from the beginning of the reaction and after the hydrogenation, base is added, the reaction mixture is filtered to separate the catalyst and the title compound recovered from the filtrate.

The processes described in the art based on asymmetric hydrogenation of imines, enamine or enamide for the synthesis of (S)-2-ethyl-N-(1-methoxypropan-2-yl)-6-methyl aniline, an important precursor in the synthesis of (S)-metolachlor, uses costly ligands as catalysts, harsh reaction conditions, additional use of other chemical additives and solvents making the process economically not viable. Further, the asymmetric hydrogenation of imines has several important drawbacks, such as the coordination of substrates, which can take place through both the nitrogen donor atom and the double bond, the E/Z isomeric mixture present in acyclic imines, and the poisoning effect of the resultant amines on the catalyst. Most importantly, the processes described in the art provide the end product with moderate optical purity, approx. ee 80%.

Keeping in view of the high biological activity of the 'S' enantiomer of Metolachlor as herbicides and the shortcomings of the prior art processes to obtain S-Metolachlor with high enantiopurity, the present inventors felt a need to provide an alternate route which is simple and effective for the preparation of (S)-2-ethyl-N-(1-methoxypropan-2-yl)-6-methyl aniline, a precursor of S-Metolachlor, with high enantiomeric excess (ee), by employing enantiopure (R)-epichlorohydrin as starting material, which will subsequently result in deriving S-Metolachlor with high ee.

Enantiopure epichlorohydrin (ECH) is a valuable epoxide intermediate for preparing optically active pharmaceuticals and other organic compounds. It undergoes various reactions with nucleophiles, electrophiles, acids, and bases because of the versatile reactivity of its epoxide ring. The present inventors have exploited the versatile reactivity of epichlorohydrin for synthesis of (S)-2-ethyl-N-(1-methoxypropan-2-yl)-6-methyl aniline with high selectivity.

OBJECTS OF INVENTION

The main objective of the present invention is to provide a simple and effective process for the preparation of (S)-2-ethyl-N-(1-methoxypropan-2-yl)-6-methyl aniline. Another objective of the present invention is to provide synthesis of (S)-2-ethyl-N-(1-methoxypropan-2-yl)-6-methyl aniline with excellent selectivity and enantiomeric excess greater than 99% from enantiopure (R)-epichlorohydrin via formation of aziridine intermediate.

SUMMARY OF THE INVENTION

Accordingly, the present invention provides a process for enantioselective preparation of (S)-2-ethyl-N-(1-methoxypropan-2-yl)-6-methyl aniline from (R)-epichlorohydrin, wherein the said process comprising the steps of;

i) refluxing solution of (R)-epichlorohydrin [(R)-2] with 2-ethyl-6-methyl aniline in mole ratio ranging between 1:1 to 1:3 in lower alcohol for a period ranging between 6-8 hours at temperature ranging between 60-80° C., followed by addition of crushed KOH to the mixture at a temperature of 0° to 25°

C., stirring vigorously at room temperature ranging between 25-35° C. to obtain (R)-1-((2-ethyl-6-methylphenyl)amino)-3-methoxypropan-2-ol [(R)-3];

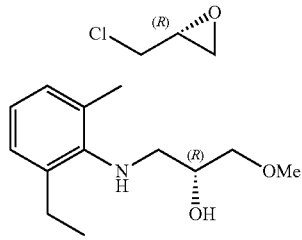

ii) adding dropwise solution of DIAD (Diisopropyl azo dicarboxylate) in dry toluene to a solution of [(R)-3] of step (i) and triphenylphosphine in dry toluene under $N_2$ atmosphere at 0-10° C., followed by refluxing at temperature ranging between 100-130° C. for a period ranging between 3-5 hrs to obtain (S)-1-(2-ethyl-6-methylphenyl)-2-(methoxymethyl) aziridine [(S)-4];

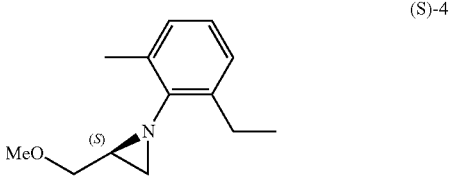

iii) catalytic hydrogenating of solution [(S)-4] of step (ii) in a solvent in presence of a catalyst under hydrogen atmosphere in the range of 30-50 psi under refluxing at temperature ranging between 20 to 30° C. for a period ranging between 1-3 hrs to obtain (S)-2-ethyl-N-(1-methoxypropan-2-yl)-6-methylaniline [(S)-1].

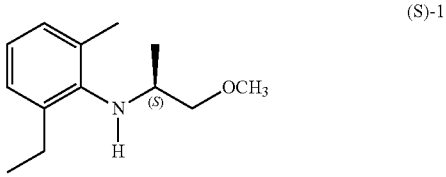

In one embodiment of the present invention the catalytic hydrogenation in step (iii) is carried out in presence of transition metals loaded on activated carbon catalyst, wherein the transition metals are selected from the group consisting of Palladium, Platinum, Rhodium, Ruthenium, Iridium, Iron or combination thereof.

In an embodiment of the present invention the transition metals loaded on activated carbon catalyst in step (iii) is in the range of 10-20 wt %.

In another embodiment of the present invention the solvent used in step (iii) is selected from alcohol, ethyl acetate, chloroform and acetic acid.

In another embodiment of the present invention said alcohol is selected from methanol, ethanol, propanol, isopropanol, t-butyl alcohol or mixtures thereof.

In another embodiment of the present invention the lower alcohol in step i) is selected from the group consisting of methanol, ethanol, pentanol, butanol, isopropanol, n-propanol, t-butyl alcohol, tert-Amyl alcohol (TAA), isoamyl alcohol, hexyl alcohol and mixtures thereof.

In another embodiment of the present invention yield of (S)-2-ethyl-N-(1-methoxypropan-2-yl)-6-methyl aniline is in the range of 92-96%.

In another embodiment of the present invention enantiomeric excess of (S)-2-ethyl-N-(1-methoxypropan-2-yl)-6-methyl aniline is in the range of 95-99%.

In another embodiment of the present invention S)-2-ethyl-N-(1-methoxypropan-2-yl)-6-methyl aniline is a precursor of Metolachlor.

DETAILED DESCRIPTION OF THE INVENTION

Figure 1:
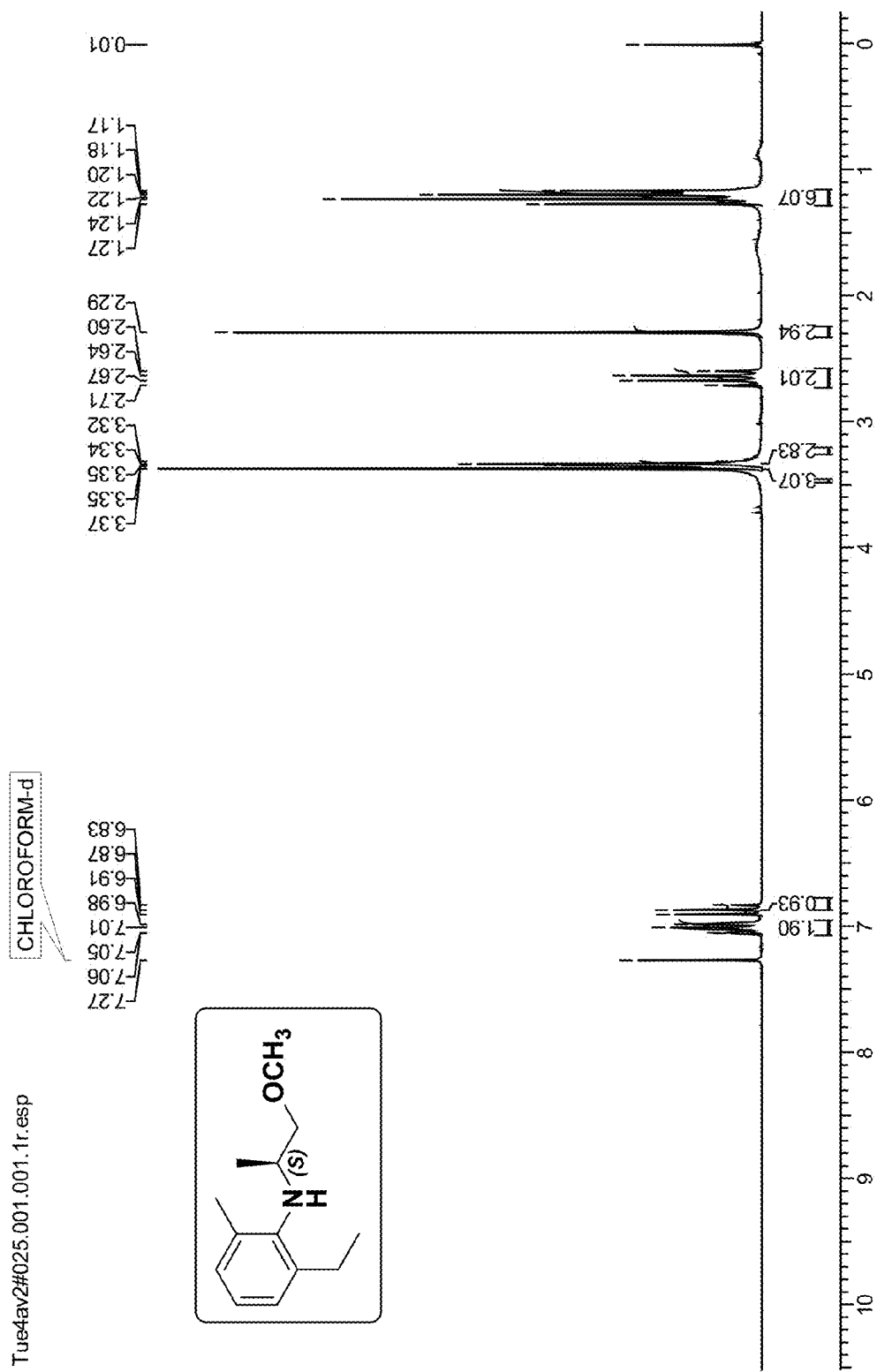
FIG. 1 depicts $^1$H NMR of (S)-2-ethyl-N-(1-methoxypropan-2-yl)-6-methylaniline [(S)-1]
Figure 2:
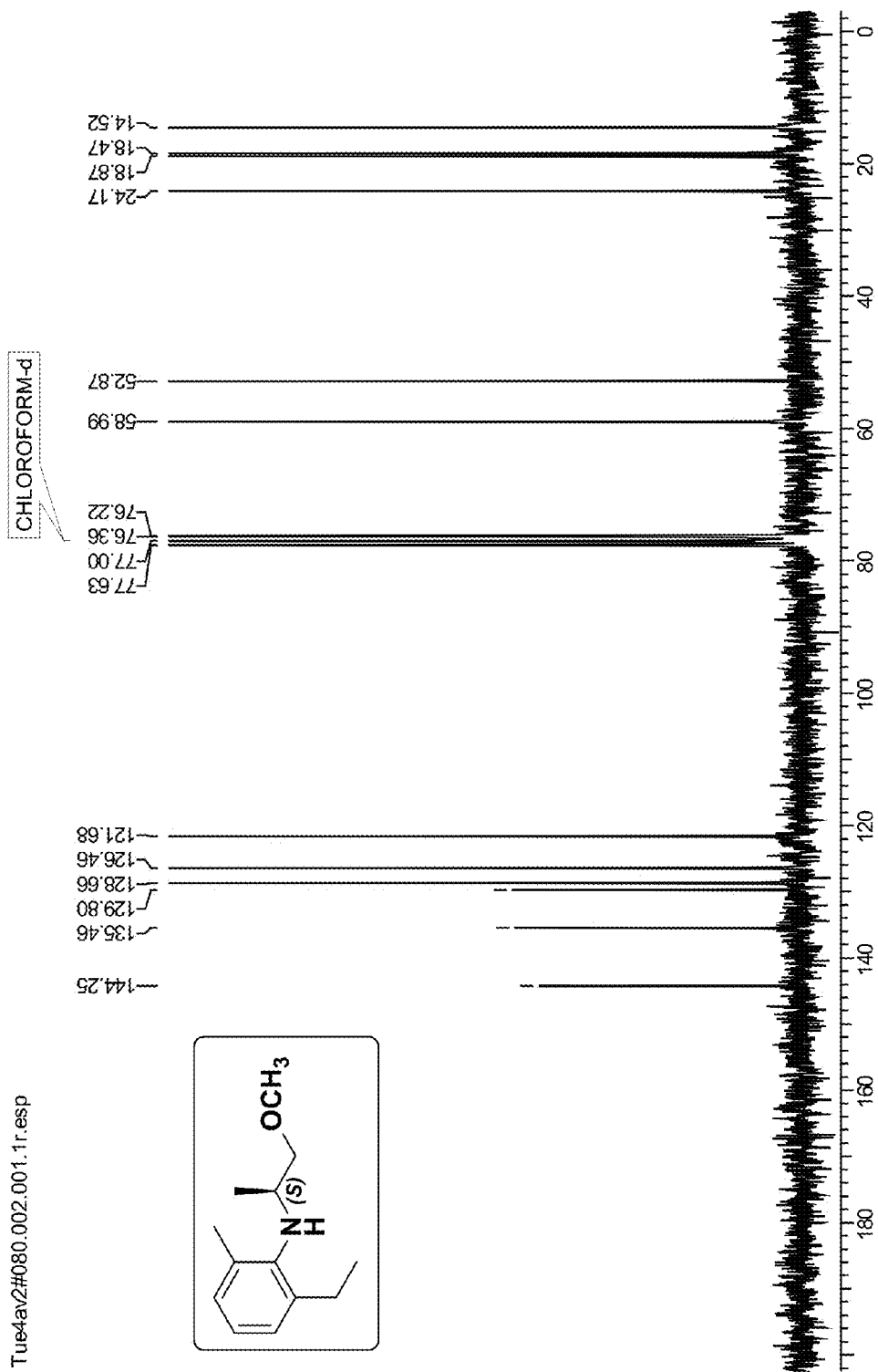
FIG. 2 depicts $^{13}$C NMR of (S)-2-ethyl-N-(1-methoxypropan-2-yl)-6-methylaniline [(S)-1]
Figure 3:
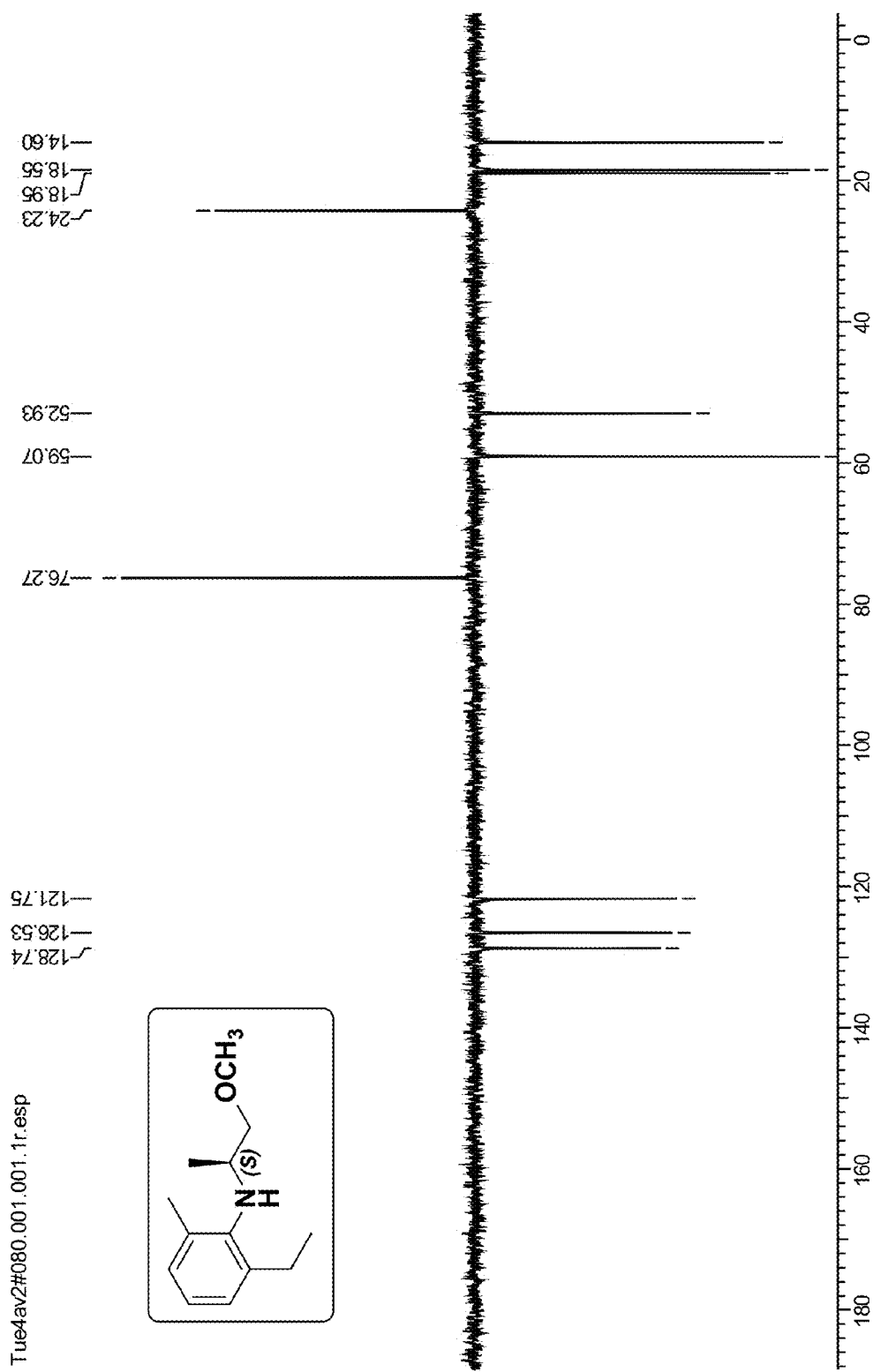
FIG. 3 depicts $^{13}$C-DEPT of (S)-2-ethyl-N-(1-methoxypropan-2-yl)-6-methylaniline [(S)-1]
Figure 4:
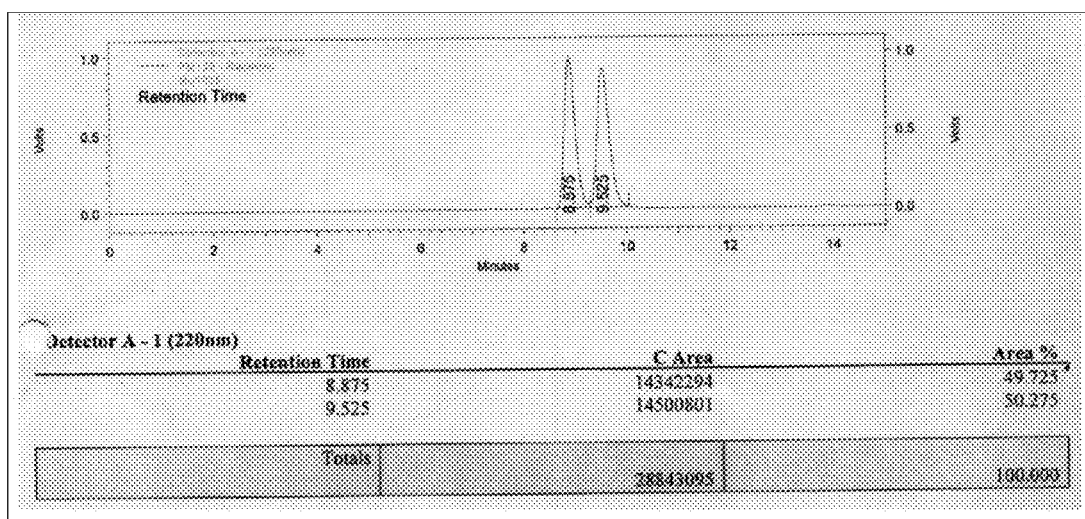
FIG. 4 depicts Chiral HPLC analysis of 2-ethyl-N-(1-methoxypropan-2-yl)-6-methylaniline (racemic)
Figure 5:
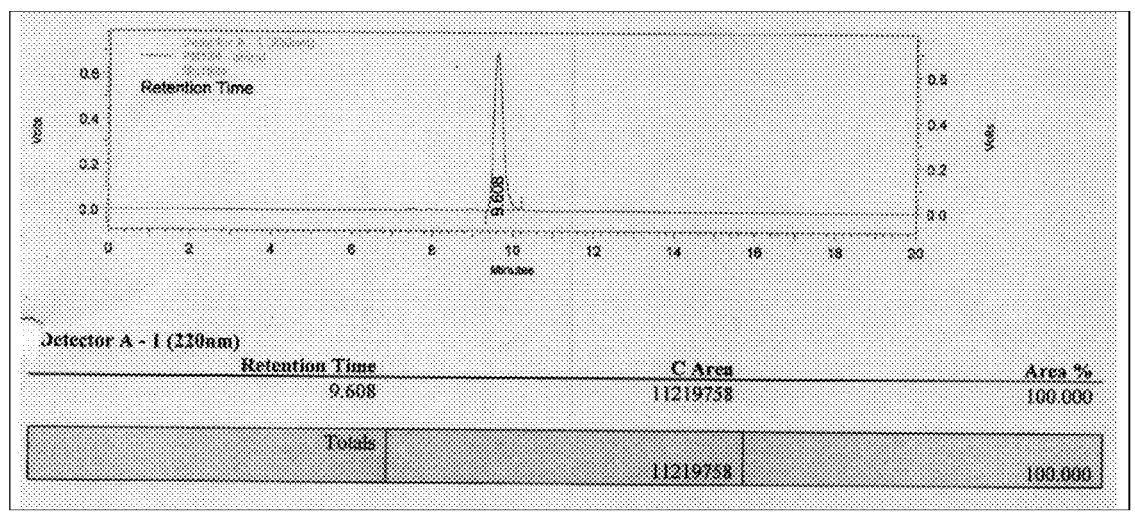
FIG. 5 depicts Chiral HPLC analysis of (S)-2-ethyl-N-(1-methoxypropan-2-yl)-6-methylaniline [(S)-1].
Figure 6:
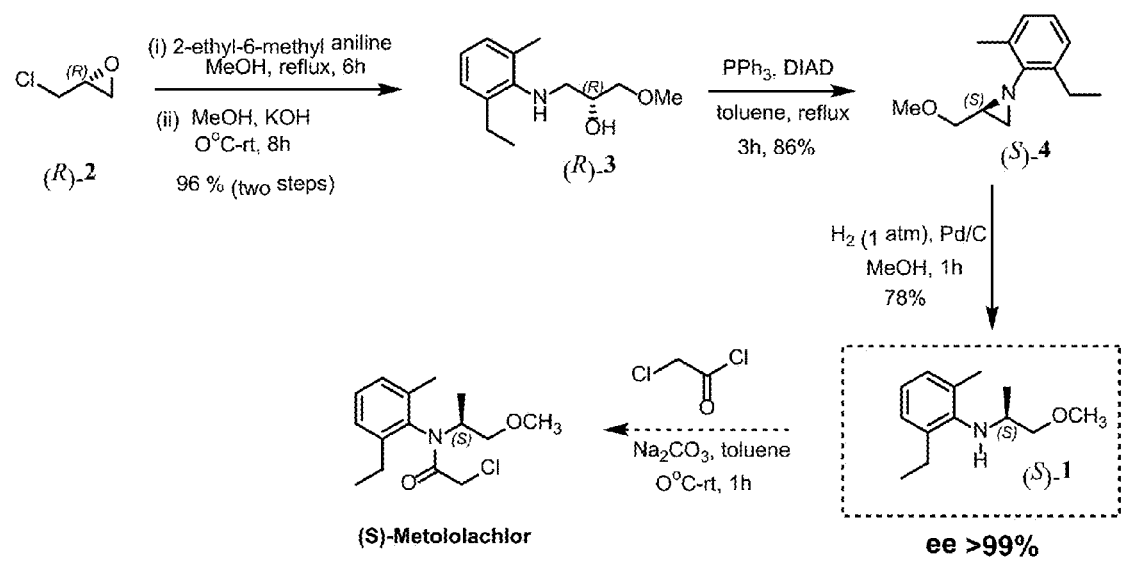
FIG. 6 Scheme: 1 Process for synthesis of (S)-2-ethyl-N-(1-methoxypropan-2-yl)-6-methylaniline (S)-1

The invention will now be described in detail in connection with certain preferred and optional embodiments, so that various aspects thereof may be more fully understood and appreciated and briefly described as follows.

The present invention provides a simple, efficient process for the preparation of (S)-2-ethyl-N-(1-methoxypropan-2-yl)-6-methyl aniline, a precursor of S-Metolachlor, with high enantiopurity starting from enantiopure (R)-epichlorohydrin via formation of aziridine intermediate, wherein the enantiopurity/optical purity of (S)-2-ethyl-N-(1-methoxypropan-2-yl)-6-methyl aniline is more than 99% ee.

In a preferred embodiment, the invention, provides a novel process for the enantioselective synthesis of (S)-2-ethyl-N-(1-methoxypropan-2-yl)-6-methyl aniline, precursor of S-Metolachlor, comprises catalytic hydrogenation of aziridine intermediate [(S)-4] in presence of a solvent to afford (S)-2-ethyl-N-(1-methoxypropan-2-yl)-6-methyl aniline [(S)-1] with high ee; wherein the solvent is selected from alcohol, acetic acid, choloroform, ethyl acetate and such like.

In an embodiment, the alcohol is selected from methanol, ethanol, propanol, isopropanol, t-butyl alcohol or mixtures thereof.

Accordingly the catalytic hydrogenation of [(S)-4] is carried out in presence of transition metals loaded on activated carbon or charcoal under hydrogen atmosphere, wherein the transition metals are selected from the group consisting of Palladium, Platinum, Rhodium, Ruthenium, Iridium, Iron or combination thereof; the catalytic hydrogenation is completed within 1-3 hrs. Further the metal catalyst (transition metals loaded on activated carbon) is used in the concentration range of 10-20 wt %.

In another preferred embodiment, the present invention provides a simple and effective enantioselective synthesis of (S)-2-ethyl-N-(1-methoxypropan-2-yl)-6-methyl aniline, a precursor of S-Metolachlor, with ee greater than 99% starting from enantiopure (R)-epichlorohydrin in organic solvent system, wherein the process comprises following steps:

i. refluxing solution of (R)-epichlorohydrin [(R)-2] in lower alcohol with 2-ethyl-6-methyl aniline for about 6-8 hours, followed by addition of crushed KOH to the mixture at a temperature of 0° to 25° C., stirring vigorously at room temperature to obtain (R)-1((2-ethyl-6-methylphenyl)amino)-3-methoxypropan-2-ol [(R)-3];

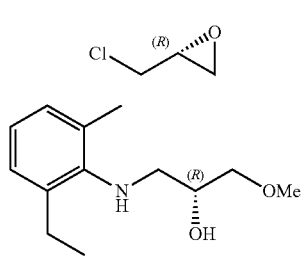

(R)-2

(R)-3 ii. adding dropwise solution of DIAD (Diisopropyl azo dicarboxylate) to a solution of [(R)-3] of step (i) and triphenylphosphine in dry toluene under $N_2$ atmosphere at 0° C., followed by refluxing to obtain (S)-1-(2-ethyl-6-methylphenyl)-2-(methoxymethyl) aziridine [(S)-4];

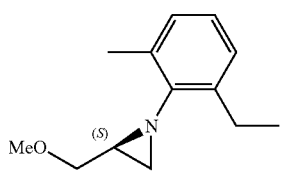

(S)-4 iii. catalytic hydrogenating of methanolic solution [(S)-4] of step (ii) in presence of Pd/C under hydrogen atmosphere to afford the desired product (S)-2-ethyl-N-(1-methoxypropan-2-yl)-6-methylaniline [(S)-1] with high ee.

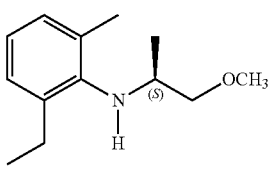

(S)-1

Further the (S)-2-ethyl-N-(1-methoxypropan-2-yl)-6-methylaniline [(S)-1] is converted into (S)-Metolachlor by the known process.

According to the invention, the schematic presentation of the instant process is given herein below in scheme 1.

The solution of (R)-epichlorohydrin [(R)-2] in lower alcohol is refluxed with 2-ethyl-6-methyl aniline for about 6 hours or till the completion of the reaction, where the completion of the reaction is monitored by TLC, followed by the addition of crushed KOH to the mixture at a temperature below 25° C., with vigorous stirring for about 8 hours at room temperature. Further the completion of the reaction is monitored by TLC, excess of lower alcohol was evaporated under reduced pressure. After evaporation the reaction mixture is poured into water and extracted with organic solvent. The combined organic layers are washed with brine and dried over $Na_2SO_4$. The solvent is evaporated and the product is purified by known technique to afford (R)-1-((2-ethyl-6-methylphenyl)amino)-3-methoxypropan-2-ol (R) [3] in high yield i.e. more than 95%.

The lower alcohol used in the instant process is not limited to methanol, ethanol, pentanol, butanol, isopropanol, n-propanol, t-butyl alcohol, tert-Amyl alcohol (TAA), isoamyl alcohol, hexyl alcohol and mixtures thereof and the organic solvent is selected from the group consisting of ethyl acetate, acetone, chloroform, toluene, pet ether, methanol, ethanol and mixtures thereof. Further the addition of the crushed KOH is carried out at the temperature range of 0° C. to 25° C., Subsequently to a solution of DIAD in dry toluene is added dropwise a solution of [(R)-3] and triphenylphosphine in dry toluene under $N_2$ atmosphere at 0° C. The reaction mixture is refluxed for 3-5 hrs. After completion of reaction monitored by TLC, the organic solvent is evaporated under reduced pressure and the residue is purified to afford (S)-1-(2-ethyl-6-methylphenyl)-2-(methoxymethyl) aziridine [(S) -4] Further alcoholic solution of [(S)-4] is added to palladium on activated carbon and the reaction mixture is stirred under hydrogen atmosphere for 1 to 3 hrs. After completion of the reaction (monitored by TLC) the catalyst is filtered over the celite bed and the solvent is evaporated under reduced pressure. The crude product is purified to afford (S)-2-ethyl-N -(1-methoxypropan-2-yl)-6-methylaniline [(S)-1]

The intermediate (S)-2-ethyl-N-(1-methoxypropan-2-yl)-6-methylaniline [(S)-1] prepared by the process of current invention is obtained with ☐99% ee and yield more than 75%.

In an another embodiment, the herbicide S-Metolachlor is prepared from (S)-2-ethyl-N-(1-methoxypropan-2-yl)-6-methylaniline [(S)-1] with ee 99% by using chloroacetyl chloride in the presence of a base in a non-polar solvent which is known in the art.

Further the intermediates and the product of the instant process are characterized by $^1H$ NMR and $^{13}C$ NMR spectra.

The following examples are given by way of illustration of the present invention and therefore should not be construed to limit the scope of the invention.

EXAMPLES

Material and Method:

Solvents were purified and dried by standard procedures prior to use. $^1H$ NMR and $^{13}C$ NMR spectra were recorded on a Bruker AC-200 & 400 NMR spectrometers. Spectra were obtained in $CDCl_3$. The reactions were monitored by using TLC plates Merck Silica Gel 60 F254 and visualization with UV light (254 and 365 nm), $KMnO_4$ and anisaldehyde in ethanol as development reagents. Optical rotations were measured with a JASCO P 1020 digital polarimeter. Enantiomeric excess was determined by chiral HPLC, performed on chiral HPLC, performed on 'SHIMADZU' SCL-10A unit system and UV monitor as detector.

Example 1

Preparation of (R)-1-((2-ethyl-6-methylphenyl) amino)-3-methoxypropan -2-ol [(R)-3]

To a stirred solution of epichlorohydrin (R)-2 (2 g, 21.6 mmol) in methanol (15 mL) was added 2-ethyl-6-methyl aniline (3.2 g, 23.7 mmol) and the resulting mixture was refluxed for 6 h at 70° C. After completion of the reaction (monitored by TLC), crushed KOH (3.0 g, 54.0 mmol) was added portion wise at temperature 10° C. After completing the addition, the reaction mixture was stirred vigorously for 8 h at 30° C. After completion of the reaction (monitored by TLC), excess methanol was evaporated under reduced pressure. The reaction mixture was then poured into water (20 mL) and extracted with EtOAc (2×15 mL). The combined organic layers were washed with brine (10 mL) and dried over $Na_2SO_4$. Evaporation of the solvent gave the crude residue which was purified by silica gel column chromatography using petroleum ether/EtOAc (90:10) as eluent to furnish (R)-1-((2-ethyl-6-methylphenyl)amino)-3-methoxypropan-2-ol (R)-3 as a pale brown oil (4.6 g, 96%); $[\alpha]^{21}{}_D$=+4.93 (c 2.09, $CHCl_3$); IR ($CHCl_3$, cm$^{-1}$): $\nu_{max}$ 3421, 3009, 2966, 1593, 1466, 1377, 1216, 1129, 968, 667; $^1$H NMR (400 MHz, $CDCl_3$): $\delta_H$ 1.26 (t, J=7.5 Hz, 3H), 2.33 (s, 3H), 2.66-2.71 (m, 2H), 2.96-3.00 (dd, J=12.4, 7 Hz, 1H), 3.09-3.12 (dd, J=12.4, 3.9 Hz, 1H), 3.42 (s, 3H), 3.46-3.49 (dd, J=9.4, 6.3 Hz, 1H), 3.50-3.53 (dd J=9.7, 3.6 Hz, 1H), 3.96-4.00 (m, 1H), 6.91 (apparent t, J=7.2 Hz, 1H), 7.01 (d, J=7.3 Hz, 1H), 7.04 (d, J=7.6 Hz, 1H); $^{13}$C NMR (100 Hz, $CDCl_3$): $\delta_C$ 145, 136.2, 130.6, 128.8, 126.7, 122.6, 75.3, 69.6, 59.2, 51.5, 24.2, 18.5, 14.8; MS: m/z 224 [M+1]$^+$, 246 [M+Na]$^+$.

Example 2

(S)-1-(2-ethyl-6-methylphenyl)-2-(methoxymethyl) aziridine [(S)-4]

A solution of Diisopropyl azodicarboxylate (DIAD) (3.0 mL, 15.4 mmol) in dry toluene (5 mL) was added dropwise to a solution of (R)-3 (2.3 g, 10.3 mmol) and triphenylphosphine (4.0 g, 15.4 mmol) in a dry toluene (25 mL) under $N_2$ atmosphere at 0° C. The reaction mixture was refluxed for 3 h 120° C. After completion of reaction (monitored by TLC), the solvent was evaporated under reduced pressure and the residue was purified by silica gel column chromatography (100-200 mesh, petroleum ether/ethyl acetate, 95:5) to afford (S)-1-(2-ethyl-6-methylphenyl)-2-(methoxymethyl)aziridine (S)-4 as a yellow oil (1.8 g, 86%). $[\alpha]^{21}{}_D$=−120. 51 (c 1.0, $CHCl_3$); IR ($CHCl_3$, cm$^{-1}$): $\nu_{max}$ 3419, 2967, 2875, 1915, 1745, 1592, 1460, 1378, 1355, 1276, 1217, 1188, 1108, 965, 929, 900, 666; $^1$H NMR (400 MHz, $CDCl_3$): $\delta_H$ 1.27 (t, J=7.6 Hz, 3H), 2.03 (d, J=6.3 Hz, 1H), 2.38 (s, 3H), 2.40 (d, J=3.0 Hz, 1H), 2.44-2.48 (m, 1H), 2.75-2.83 (m, 2H), 3.46 (s, 3H), 3.48-3.51 (dd, J=10.4, 5.7 Hz, 1H), 3.91-3.94 (dd, J=10.3, 4.4 Hz, 1H), 6.87 (apparent t, J=7.6 Hz, 1H), 6.95 (d, J=7.2 Hz, 1H), 7.01 (d, J=7.6 Hz, 1H); $^{13}$C NMR (100 MHz, $CDCl_3$): $\delta_C$ 149.9, 134.9, 129.1, 128.8, 126.9, 122.6, 74.0, 59.1, 39.4, 34.9, 24.3, 19.3, 14.3; MS: m/z 206 [M+1]$^+$, 228 [M+Na]$^+$.

Example 3

(S)-2-ethyl-N-(1-methoxypropan-2-yl)-6-methylaniline [(S)-1]

To a solution of (S)-4 (1.0 g, 4.87 mmol) in methanol (10 mL) was added palladium on activated carbon (0.065 g, 10%) and the reaction mixture was stirred under hydrogen atmosphere (balloon) 30 psi for 1 h at 30° C. After completion of the reaction (monitored by TLC) the catalyst was filtered over the celite bed (EtOAc eluent) and the solvent was evaporated under reduced pressure. The crude product was purified by silica gel column chromatography (100-200 mesh, petroleum ether/ethyl acetate, 98:2) to afford (S)-2-ethyl-N-(1-methoxypropan-2-yl)-6-methylaniline (S)-1 (0.79 g, 78%) as a pale yellow oil; $[\alpha]21^1{}_D$=+11.68 (c 2.0, $CHCl_3$); ee>99% [Chiral HPLC analysis: Chiralcel OD-H (250×4.6 mm) column; eluent: n-hexane/isopropanol=99.75:0.25; flow rate: 0.5 mL/min; detector: 220 nm]; IR ($CHCl_3$, cm$^{-1}$): $\nu$ max 3409, 3019, 2969, 2877, 2401, 1593, 1465, 1385, 1215, 1103, 928, 669. $^1$H NMR (200 MHz, $CDCl_3$): $\delta_H$ 1.18 (d, J=6.4 Hz, 3H), 1.25 (t, J=7.5 Hz, 3H), 2.29 (s, 3H), 2.65 (q, J=7.3 Hz, 2H), 3.35-3.37 (m, 3H), 3.38 (s, 3H), 6.88 (apparent t, J=7.4 Hz, 1H), 6.98-7.06 (m, 2H); $^{13}$C NMR (50 Hz, $CDCl_3$): $\delta_C$ 144.2, 135.5, 129.8, 128.7, 126.5, 121.7, 76.2, 58.9, 52.9, 24.2, 18.9, 18.5, 14.5; MS: m/z 208 [M+1]$^+$, 230 [M+Na]$^+$.

ADVANTAGES OF INVENTION

The present invention is advantageous over the prior arts, as the enantioselective process of the instant invention succeeds in providing the important precursor (S)-2-ethyl -N-(1-methoxypropan-2-yl)-6-methylaniline of S-Metolachlor with high enantiopurity (ee>99%) by employing simple, efficient and industrially viable process. Also the starting material i.e. (R)-epichlorohydrin is commercially available. In the instant process highly enantiopure/optically pure precursor of Metolachlor gives highly pure enantiomer of Metolachlor i.e. (S)-Metolachlor having significant herbicidal activity.

The invention will now be illustrated with help of examples. The aforementioned embodiments and below mentioned examples are for illustrative purpose and are not meant to limit the scope of the invention. Various modifications of aforementioned embodiments and below mentioned examples are readily apparent to a person skilled in the art. All such modifications may be construed to fall within the scope and limit of this invention as defined by the appended claims.

We claim:

1. A process for enantioselective preparation of (S)-2-ethyl-N-(1-methoxypropan-2-yl)-6-methyl aniline [(S)-1] from (R)-epichlorohydrin, wherein the process comprises the steps of:

i) refluxing a solution of (R)-epichlorohydrin [(R)-2] with 2-ethyl-6-methyl aniline in mole ratio ranging between 1:1 to 1:3 in lower alcohol for a period ranging between 6-8 hours at temperature ranging between 60-80° C., followed by addition of crushed KOH to the mixture at a temperature of 0° to 25° C., stirring vigorously at room temperature ranging between 25-35° C. to obtain (R)-1-((2-ethyl-6-methylphenyl)amino)-3-methoxypropan-2-ol [(R)-3];

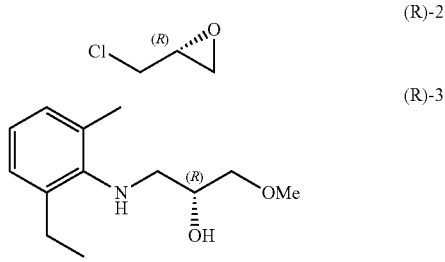

ii) adding dropwise solution of DIAD (Diisopropyl azo dicarboxylate) in dry toluene to a solution of [(R)-3] of step (i) and triphenylphosphine in dry toluene under $N_2$ atmosphere at 0-10° C., followed by refluxing at temperature ranging between 100-130° C. for a period ranging between 3-5 hours to obtain (S)-1-(2-ethyl-6-methylphenyl)-2-(methoxymethyl) aziridine [(S)-4];

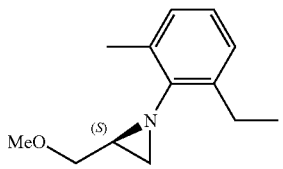
(S)-4 iii) catalytic hydrogenating of solution [(S)-4] of step (ii) in a solvent in presence of a catalyst under hydrogen atmosphere in the range of 30-50 psi under refluxing at temperature ranging between 20 to 30° C. for a period ranging between 1-3 hours to obtain (S)-2-ethyl-N-(1-methoxypropan-2-yl)-6-methylaniline [(S)-1]:

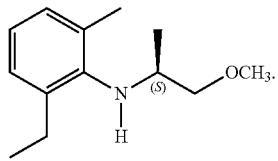
(S)-1

2. The process according to claim 1, wherein the catalytic hydrogenation in step (iii) is carried out in presence of transition metals loaded on activated carbon catalyst, wherein the transition metals are selected from the group consisting of Palladium, Platinum, Rhodium, Ruthenium, Iridium, Iron, and combinations thereof.

3. The process according to claim 1, wherein the transition metals loaded on activated carbon catalyst in step (iii) is in the range of 10-20 wt %.

4. The process according to claim 1, wherein the solvent used in step (iii) is selected from the group consisting of alcohol, ethyl acetate, chloroform, and acetic acid.

5. The process according to claim 4, wherein said alcohol is selected from the group consisting of methanol, ethanol, propanol, isopropanol, t-butyl alcohol, and mixtures thereof.

6. The process according to claim 1, wherein the lower alcohol in step i) is selected from the group consisting of methanol, ethanol, pentanol, butanol, isopropanol, n-propanol, t-butyl alcohol, tert-Amyl alcohol (TAA), isoamyl alcohol, hexyl alcohol and mixtures thereof.

7. The process according to claim 1, wherein yield of (S)-2-ethyl-N-(1-methoxypropan-2-yl)-6-methyl aniline is in the range of 92-96%.

8. The process according to claim 1, wherein enantiomeric excess of (S)-2-ethyl-N-(1-methoxypropan-2-yl)-6-methyl aniline is in the range of 95-99%.

9. The process according to claim 1, wherein S)-2-ethyl-N-(1-methoxypropan-2-yl)-6-methyl aniline is a precursor of Metolachlor.

* * * * *